United States Patent
Törmälä et al.

(10) Patent No.: US 6,692,499 B2
(45) Date of Patent: *Feb. 17, 2004

(54) SURGICAL FASTENER FOR TISSUE TREATMENT

(75) Inventors: Pertti Törmälä, Tampere (FI); Timo Pohjonen, Tampere (FI); Markku Tamminmaki, Tampere (FI)

(73) Assignee: Linvatec Biomaterials Oy, Tampere (FI)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/887,130

(22) Filed: Jul. 2, 1997

(65) Prior Publication Data

US 2002/0058966 A1 May 16, 2002

(51) Int. Cl.⁷ ................................................ A61B 17/56
(52) U.S. Cl. ............................ 606/72; 606/75; 606/76; 411/452
(58) Field of Search .................. 606/77, 76, 72, 606/88, 86, 104, 60–75, 94, 95, 232, 233; 623/14, 16; 411/439, 457, 452

(56) References Cited

U.S. PATENT DOCUMENTS

| | | |
|---|---|---|
| 1,206,425 A | 11/1916 | Feasey |
| 1,311,903 A | 8/1919 | Leschander |
| 1,949,111 A | 2/1934 | Randall |
| 2,570,465 A | 10/1951 | Lundholm |
| 2,631,854 A | 3/1953 | Volman |
| 3,123,077 A | 3/1964 | Aleamo |
| 3,166,072 A | 1/1965 | Sullivan |
| 3,236,142 A | 2/1966 | Bradway |
| 3,593,342 A | 7/1971 | Niebauer et al. |
| 3,636,956 A | 1/1972 | Schneider |

(List continued on next page.)

FOREIGN PATENT DOCUMENTS

| | | |
|---|---|---|
| DE | 27 40 274 B2 | 4/1980 |
| EP | 0 146 398 | 6/1985 |
| EP | 0 454 645 | 10/1991 |
| EP | 0 513 736 | 11/1992 |
| EP | 0 526 682 | 2/1993 |

(List continued on next page.)

OTHER PUBLICATIONS

Lieutenant Colonel Robet W. Augustine et al., Boat–Nail Fixation of Tendons and Ligaments to Cancellous Bone, The Journal of Bone and Joint Surgery, vol. 38–A, No. 5, Oct. 1956.

(List continued on next page.)

Primary Examiner—Julian W. Woo
(74) Attorney, Agent, or Firm—Kenyon & Kenyon (57) ABSTRACT

The present invention relates to a surgical fastener or device (implant) formed in the shape of an arrow comprising a shaft with a proximal (first) portion having protrusions and a blunt end and a distal (second) portion having protrusions and a pointed end, the protrusions of the proximal and distal portions configured to lock the implant in a position inside a soft and/or tough tissue according to the use of the implant. The implant may be manufactured of a polymer or a polymeric compound which is substantially (bio)absorbable in tissue conditions and contains oriented reinforcing structure or the like of a polymer or polymeric compound or ceramic bioglass compound. The surgical implant of the invention is particularly but not solely intended to be used in repair surgery of traumas of soft and/or tough tissues containing fibrous structures, such as knee meniscal tissues.

9 Claims, 10 Drawing Sheets

U.S. PATENT DOCUMENTS

| | | | |
|---|---|---|---|
| 3,646,615 A | * | 3/1972 | Ness .................................. 3/1 |
| 3,716,058 A | | 2/1973 | Tanner |
| 3,757,629 A | | 9/1973 | Schneider |
| 3,867,728 A | | 2/1975 | Stubstad et al. |
| 3,892,232 A | | 7/1975 | Neufeld |
| 3,946,740 A | | 3/1976 | Bassett |
| 3,960,152 A | | 6/1976 | Augurt et al. |
| 3,981,051 A | | 9/1976 | Brumlik |
| 4,006,747 A | | 2/1977 | Kronenthal et al. |
| 4,060,089 A | | 11/1977 | Noiles |
| 4,259,959 A | | 4/1981 | Walker |
| 4,263,903 A | | 4/1981 | Griggs |
| 4,313,232 A | | 2/1982 | Habal et al. |
| 4,316,469 A | | 2/1982 | Kapitanov |
| 4,402,445 A | | 9/1983 | Green |
| 4,451,397 A | | 5/1984 | Huc et al. |
| 4,454,875 A | | 6/1984 | Pratt et al. |
| 4,532,926 A | | 8/1985 | O'Holla |
| 4,548,202 A | | 10/1985 | Duncan |
| 4,634,445 A | | 1/1987 | Helal |
| 4,635,637 A | | 1/1987 | Schreiber |
| 4,655,777 A | | 4/1987 | Dunn et al. |
| 4,669,473 A | | 6/1987 | Richards et al. |
| 4,688,561 A | | 8/1987 | Reese |
| 4,743,257 A | | 5/1988 | Tormala et al. |
| 4,873,976 A | | 10/1989 | Schreiber |
| 4,884,572 A | | 12/1989 | Bays et al. |
| 4,895,141 A | | 1/1990 | Koeneman et al. |
| 4,895,148 A | | 1/1990 | Bays et al. |
| 4,898,186 A | | 2/1990 | Ikada et al. |
| 4,924,865 A | | 5/1990 | Bays et al. |
| 4,935,028 A | | 6/1990 | Drews |
| 4,968,317 A | | 11/1990 | Tormala et al. |
| 4,976,715 A | * | 12/1990 | Bays et al. .................. 606/77 |
| 5,013,316 A | | 5/1991 | Goble et al. |
| 5,053,047 A | | 10/1991 | Yoon |
| 5,059,206 A | | 10/1991 | Winters |
| 5,092,896 A | | 3/1992 | Meuli et al. |
| 5,102,421 A | | 4/1992 | Anspach, Jr. |
| 5,108,443 A | | 4/1992 | Branemark |
| 5,129,906 A | | 7/1992 | Ross et al. |
| 5,201,766 A | | 4/1993 | Georgette |
| 5,203,864 A | | 4/1993 | Phillips |
| 5,207,712 A | | 5/1993 | Cohen |
| 5,236,431 A | * | 8/1993 | Gogolewski et al. ......... 606/72 |
| 5,246,441 A | | 9/1993 | Ross et al. |
| 5,261,914 A | * | 11/1993 | Warren ........................ 606/73 |
| 5,312,360 A | | 5/1994 | Behl |
| 5,370,646 A | | 12/1994 | Reese et al. |
| 5,374,268 A | * | 12/1994 | Sander ......................... 606/72 |
| 5,376,118 A | | 12/1994 | Kaplan et al. |
| 5,398,861 A | | 3/1995 | Green |
| 5,425,747 A | | 6/1995 | Brotz |
| 5,425,766 A | | 6/1995 | Bowald |
| 5,480,447 A | | 1/1996 | Skiba |
| 5,505,735 A | | 4/1996 | Li |
| 5,507,823 A | | 4/1996 | Walston et al. |
| 5,514,181 A | | 5/1996 | Light et al. |
| 5,522,843 A | * | 6/1996 | Zang ......................... 606/232 |
| 5,534,033 A | | 7/1996 | Simpson |
| 5,549,676 A | | 8/1996 | Johnson |
| 5,562,704 A | * | 10/1996 | Tamminmaki et al. ...... 606/213 |
| 5,569,252 A | | 10/1996 | Justin et al. |
| 5,569,264 A | | 10/1996 | Tamminmaki et al. |
| 5,601,558 A | * | 2/1997 | Torrie et al. .................. 606/72 |
| 5,643,319 A | | 7/1997 | Green |
| 5,672,178 A | * | 9/1997 | Petersen ...................... 606/75 |
| 5,683,466 A | | 11/1997 | Vitale |
| 5,702,472 A | | 12/1997 | Huebner |
| 5,720,766 A | | 2/1998 | Zang et al. |
| 5,827,298 A | | 10/1998 | Hart et al. |
| 5,843,084 A | | 12/1998 | Hart et al. |
| 5,980,524 A | * | 11/1999 | Justin et al. .................. 606/75 |

FOREIGN PATENT DOCUMENTS

| | | |
|---|---|---|
| EP | 0 423 155 B1 | 11/1994 |
| EP | 0 700 354 | 5/1997 |
| EP | 0 773 008 | 5/1997 |
| FI | 80605 | 5/1988 |
| FR | 2 458 275 | 1/1981 |
| FR | 2 712 486 | 5/1995 |
| WO | WO 85 01210 | 3/1985 |
| WO | WO 85/03857 | 9/1985 |
| WO | WO 88 05312 | 7/1988 |
| WO | WO 89 03663 A1 | 5/1989 |
| WO | WO 90 12550 | 11/1990 |
| WO | WO 91 16014 A1 | 10/1991 |
| WO | WO 93 14705 | 8/1993 |
| WO | WO 94 13228 | 6/1994 |
| WO | WO 95 22359 | 8/1995 |
| WO | WO 96 21628 | 7/1996 |
| WO | WO 96 24310 | 8/1996 |
| WO | WO 96 41596 | 12/1996 |
| WO | WO 97/18762 | 5/1997 |

OTHER PUBLICATIONS

Robert W. Augustine, M.D., Repair of the Dislocated Shoulder Using the Modified Magnuson Technic, American Journal of Surgery, vol. 91, May 1956.

Warren Stone Bickham, The Operative Technic Involved in the Operations of General and Specific Surgery, Operative Surgery, vol. II.

Cato T. Laurencin et al., Use of Polyphosphazenes for Skeletal Tissue Regeneration, Journal of Biomedical Materials Research, vol. 27, pp. 963–973 (1993).

Medical Data International, Inc., Orthopedic and Musculoskeletal Markets: Biotechnology and Tissue Engineering, Feb. 1997, at ES 1–18 and 1–28.

N.A. Palmeri et al., The Development and Testing of the Arthroscopic Meniscal Staple, Arthrocopy, vol. 5, N. 2, 1989, p. 156.

S. Vainionpaa et al., Surgical Applications of Biodegradable Polymers in Human Tissues, Progr. Polym. Sci. 14 (1989), pp. 679–716.

Search Report for International Application No. PCT/EP98/03030.

Ashammakhi et al., Strength retention of self–reinforced polyglycolide membrane; an experimental study, Biomaterials 16 (1995), pp. 135–138.

Search Report for PCT/FI 96/00351.

Search Report for Finnish Patent Application 952884.

Sasserath et al., Acta Stomatologica, Belica 88, No. 1 (1991), pp. 5–11 (See English language summary on p. 10).

Search Report for International Counterpart Application PCT/EP98/04183.

* cited by examiner

SURGICAL FASTENER FOR TISSUE TREATMENT

This application is a continuation application of application Ser. No. 08/887,130 filed Jul. 2, 1997, abandoned, the entire disclosure of which is incorporated by reference.

FIELD OF THE INVENTION

The present invention relates to a surgical fastener or device (implant) formed in the shape of an arrow comprising a shaft with a proximal (first) portion having protrusions and a blunt end and a distal (second) portion having protrusions and a pointed end, the protrusions of the proximal and distal portions configured to lock the implant in a position inside a soft and/or tough tissue according to the use of the implant. The implant may be manufactured of a polymer or a polymeric compound which is substantially (bio)absorbable in tissue conditions and contains oriented reinforcing structure or the like of a polymer or polymeric compound or ceramic bioglass compound.

The surgical implant of the invention is particularly but not solely intended to be used in repair surgery of traumas of soft and/or tough tissues containing fibrous structures, such as knee meniscal tissues.

BACKGROUND ART

With reference to the prior art in the field it has been shown that fixation of meniscus traumas like ruptures and lesions by suturing with absorbable sutures gives better results than removal of traumatized meniscal tissue, see e.g. N. A. Palmeri, T. F. Winters, A. E. Joiner and T. Evans, "The Development and Testing of the Arthroscopic Meniscal Staple", Arthroscopy, Vol. 5, No. 2, 1989, p. 156 (Ref. 1). However, arthroscopic suturing is a complicated and tedious technique where risks for the patient are significant because of danger to vessels and nerves. Additionally, the suturing of meniscus ruptures leaves a single or several loops of sutures, which can irritate joint cavity tissues. Therefore, for a long time surgeons have desired an absorbable meniscus lesion fixation device, like a staple or fastener, which has the advantages of absorbable suturing techniques but which can be used more rapidly and safely than sutures.

Several research groups have tried to develop absorbable meniscus lesion fixation devices such as clamps. However, the various demands upon such a device are high. It must be strong enough to maintain good contact of lesion tissues after the operation so that rapid healing occurs. The device must retain its strength long enough for good healing. It must be absorbed without causing complications that would prevent the healing of the lesion. Additionally, the installation of the device should be easy and rapid and should cause minimum operational trauma. Because of these high demands, an optimal absorbable meniscus lesion fixation device has not been developed yet. Palmeri et al. reported in Ref. 1 the development of a method of meniscal repair using arthroscopically applied absorbable fasteners. However, the reported method was complicated because the final design used cannulation of the staple for needle-guided placement. Additionally, staple fracture, migration and articular abrasion was found.

With regard to implants known in this field, reference is made to U.S. Pat. No. 4,873,976 which discloses an arrow-like implant particularly intended for the surgical repair of meniscal ruptures. However, the arrow-like implant according to this publication has the disadvantage that particularly its proximal end (stem) is shaped as a plate in a way that the direction of the main plane of the plate is perpendicular to the longitudinal direction of the arrow's body. Because of this fact, it is particularly difficult to install the implant, because the channel used to install the implant must have the cross-sectional shape of the stem; it is difficult to guide the implant in the installation channel, because the guiding effect is substantially brought upon the stem only, and not the body of the arrow. Furthermore, the structure of the stem causes tissue irritation and abrasion, particularly when placed in connection with the meniscus because the stem is usually left protruding to a high degree from the outer surface of the meniscus.

Bays et al. (U.S. Pat. Nos. 4,884,572 and 4,895,141) describe a surgical-repair tack and applicator and method of using them. The tack has a barb member, a shaft portion and a grip portion. The tack is made of biodegradable material having a degradation time selected to coincide with the healing time of the tissue. In an alternate embodiment, the tack's barb comprises a continuous helical barb. A disadvantage of this tack is that the grip portion is bulky and may remain on meniscal surface causing irritation inside a joint cavity.

The method and apparatus for repairing a meniscal tear disclosed by Winters (U.S. Pat. No. 5,059,206) comprises a fastener having protrusions or barbs that is applied to a meniscal tear with a delivery device. The delivery device has a flexible tip that is manipulable through a curved radius to enable the surgeon to insert the device into the central part of the knee and then extend the fastener radially outward into and across a meniscal tear. Also in this case the proximal end of the fastener is bulky and protrudes partially above and/or below the outer surface of the meniscus.

Tamminmaki et al. (U.S. Pat. No. 5,562,704) disclose an arrow-like bioabsorbable implant particularly intended for the surgical repair of meniscal ruptures. This implant does not have the guiding or abrasion problems that implants of U.S. Pat. No. 4,873,976 or U.S. Pat. No. 5,059,206 may have. However, a disadvantage of U.S. Pat. No. 5,562,704 is that the proximal part of the implant (the wings) preferably remains on the surface of the meniscus, so that when the wings break as a consequence of bioabsorption, the broken wings may irritate knee joint tissues. If the proximal part with the wings is desired to be located inside of meniscal tissue, the surface capsule of the meniscus must be cut horizontally with a special cutting blade. This lengthens the operation time and causes substantial damage to the meniscus surface.

U.S. Pat. No. 5,569,252 describes a fastener, an installation device, and method for repairing tears in the soft tissue of a patient, including meniscal tears. The fastener has a variable-pitch helical protrusion along a central portion that decreases from the distal end to the proximal end, which can serve to bring two sides of the tear into apposition as the fastener is advanced across the two sides of the tear in a screwing motion. This implant, which needs a screwing motion for installation, is slow and tedious to use arthroscopically and the turning of the implant through fibrous tissue, such as meniscus tissue, has the risk that the fibrous tissue may twist around the turning implant, hindering or preventing the installation of the implant.

Orthopedic and Musculoskeletal Markets Biotechnology and Tissue Engineering, Medical Data International, Inc., Irvine, Calif., USA, February 1997, p. 1–17 describes a bioabsorbable device for meniscal repair. This device has two legs with molded barbs that are attached by a flexible member composed of resorbable suture. The device is installed into a meniscus with an arthroscopical tool so that the legs penetrate the rupture of meniscus to hold the edges together. The disadvantage of this device is that the suture loop remains on the surface of meniscus where it can cause irritation. Additionally, the two-leg device requires a bulky installation tool which makes arthroscopical installation of the device difficult.

SUMMARY OF THE INVENTION

It is an object of the present invention to provide a bioabsorbable fastener that allows a minimally invasive method for repairing a tear in soft or tough tissue.

It is a further object to provide such a fastener that is rapid and easy to install and gives a strong and safe fixation of the tissue tear and that may be made from a nontoxic, biocompatible bioabsorbable polymer, polymer alloy or fiber reinforced polymer composite, specially designed to maintain its structural integrity during the healing of the tear and to prevent tissue abrasion.

It is an additional object to provide such a fastener having a shape designed to compress the tear.

It is a further object to provide a device (fastener) which will be shot totally inside of soft or tough tissue, like meniscal tissue, to penetrate the tissue (meniscal) tear and to hold the ruptured edges together.

These and other objects are attained with the fastener of the present invention.

The fastener of the present invention is designed for repairing a tear in soft and/or tough tissue of a patient, such as a tear of the meniscus within the knee.

The implant has a shaft with a proximal (first) portion formed with protrusions in relation to the surface of the shaft and having a blunt end and a distal (second) portion formed with protrusions in relation to the surface of the shaft and having a pointed end. The purpose of the protrusions is to arrest (lock) the implant inside of the soft and/or tough tissue after installation.

Accordingly protrusions emerge from both the proximal and distal portions of the device. The protrusions are typically barbs, scales, threads, serrations, ridges or the like. The protrusions at the distal portion of the shaft of the device prevent the installed device from slipping out of the meniscal tissue in the direction opposite to the direction of installation and the protrusions at the proximal portion of the shaft prevent the installed device from further penetrating the meniscal tissue in the direction of installation. This behavior is achieved with the special geometry of the protrusions.

In a preferred embodiment the protrusions of the distal portion of the shaft of the device are formed so that they facilitate the slipping of the device into the meniscus during insertion but they resist the slipping of the device in the direction opposite to the installation direction. On the other hand, the protrusions of the proximal portion of the shaft of the device are formed so that they stop the device inside of meniscal tissue when the device has been shot into the meniscus with the delivery (installation) tool. Both sets of protrusions, acting together, exert an advantageous compression to the ruptured surface when the device is shot into the meniscus and across the rupture. This compression serves to close the rupture and promotes healing.

A further advantageous feature of the device is that the surface of the shaft may include longitudinal ridges.

Protrusions that are manufactured on these ridges are more effective at preventing unwanted movement of the installed fastener and maintaining compression of the rupture. Because of their increased prominence, it is also easier to manufacture protrusions on ridges. Moreover, the ridges unexpectedly promote healing of the rupture by providing channels along the interiors of the ridges through which beneficial blood flow can occur along the length of the device. These channels, which are about 0.05–0.5 mm wide, act as capillaries, transporting blood from the highly vascularized distal portion of the meniscus to the poorly vascularized proximal portion of the meniscus. Further, the ridges help to guide the fastener through the cannula of the installation instrument and into the meniscal or other soft tissue during installation.

BRIEF DESCRIPTION OF THE DRAWINGS

FIG. 3A illustrates, as viewed longitudinally from the side.

FIGS. 11A–11D illustrate a method for installing fasteners of the present invention into ruptured meniscal tissue.

FIG. 12 and FIG. 13 illustrate the fibrous structure of the meniscus. For example.

FIG. 14 illustrates a meniscal cross-section, and in FIG. 15 the fastener—horizontal collagen fiber relationship is viewed from the direction from which the fastener of the present invention enters the meniscus.

DETAILED DESCRIPTION OF THE PREFERRED EMBODIMENTS

A description of the preferred embodiments of the present invention is presented with reference to FIGS. 1–15.

The preferred exemplary embodiment of the present invention comprises a fastener and method for repairing a soft or tough, tissue, like a knee meniscal tear in a human patient.

Figure 1A:
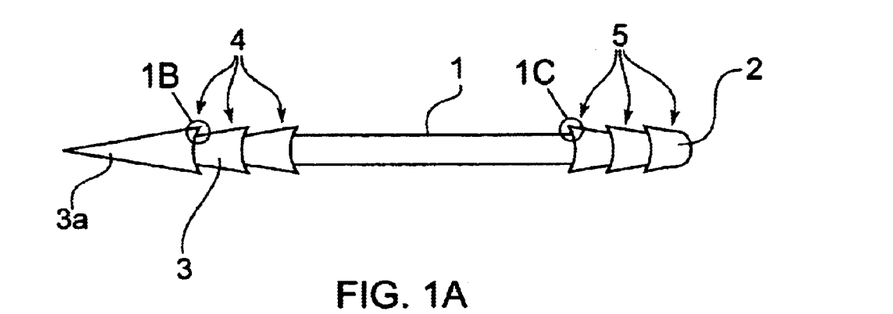
FIG. 1A illustrates, as viewed from the side, an embodiment of the present invention having an arrow shape.
Figure 1B:
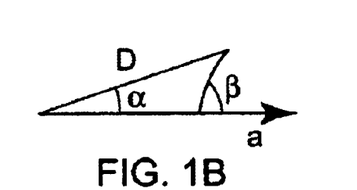
FIG. 1B illustrates a distal protrusion of FIG. 1A.
Figure 1C:
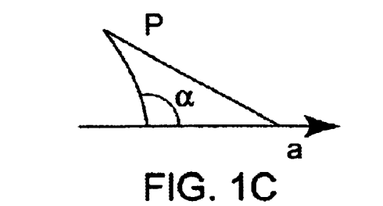
FIG. 1C illustrates a proximal protrusion of FIG. 1A.

FIG. 1 illustrates, as viewed from the side, a preferred embodiment of the fastener. It is designed to have an arrow shape, and it comprises a shaft 1, whose proximal portion 2 is formed with a blunt end for the purpose of providing the impact surface required for the instrument used in the installation of the implant and whose distal portion 3 is formed with a head with a sharp tip 3a. The distal portion comprises distal protrusions 4 with respect to the shaft 1. The distal protrusions are here sharp-profile threads which go around the shaft. The purpose of the proximal portion 2 is to stop the implant inside of the meniscus, typically just below the surface of the meniscus during the final stage of the installation. To fulfill this task, the proximal portion 2 is equipped with proximal protrusions 5, which stop the device and prevent its further sinking into the meniscus, when the pushing effect of the delivery tool stops. FIG. 1B illustrates the cross-section of a distal protrusion showing that the angle $\alpha$ between a tangent to the distal surface of the protrusion (D) and the longitudinal axis (a) of the fastener in the proximal direction is relatively small, less than 45° and preferably less than 30° to facilitate the easy penetration of the tip of the fastener into the meniscal tissue. On the other hand, the angle $\beta$ between a tangent to the proximal surface of the protrusion (D) and the axis (a) in the proximal direction is <90° to guarantee the effective prevention of slipping of the fastener back in the direction opposite to the installation direction after installation of the fastener. On the other hand, according to FIG. 1C, in the case of the proximal protrusion, P, the value of angle $\gamma$ is big (>90°) to create a strong locking force, which stops the fastener inside of the meniscal tissue after the installation procedure.

Accordingly, the proximal and distal protrusions 5 and 4 effectively lock the device inside of the meniscus preventing its movement both in the direction of installation and in the direction opposite to it. Additionally, the installation compresses the rupture surface (see FIGS. 11A–D) because the proximal protrusions 5 push the proximal side of the rupture against the distal side of the rupture during the final phase of installation.

Because the whole device is located inside of the meniscus and the proximal end of the device is relatively small, the risks of prior art devices regarding the complications originating from the presence of the bulky proximal part of the device on the meniscal surface, are eliminated.

Figure 2:
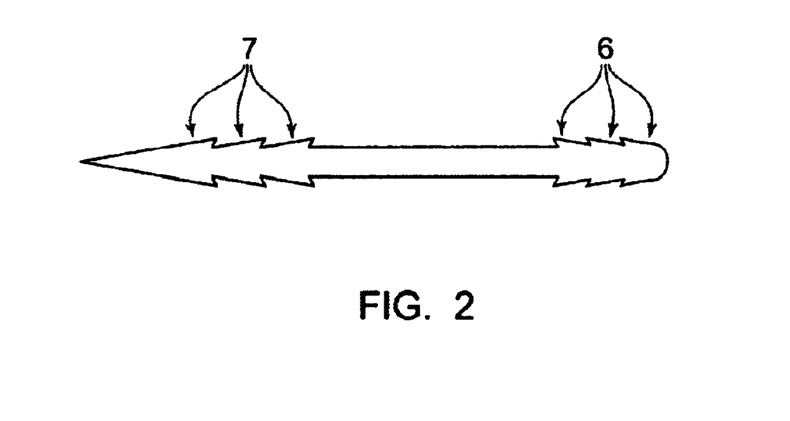
FIG. 2 illustrates another embodiment of the present invention wherein proximal protrusions and distal protrusions comprise a plurality of small barbs emerging from the surface of the proximal and distal portions of the shaft.

FIG. 2 illustrates another preferred embodiment of the fastener. Here the proximal protrusions (6) and the distal protrusions (7) comprise a plurality of small barbs emerging from the surface of the proximal and distal portions of the shaft. The fasteners of FIGS. 1 and 2 can be pushed into meniscal tissue through a cannula with a circular cross-section, which makes the manufacturing of the cannula relatively easy.

Figure 3A:
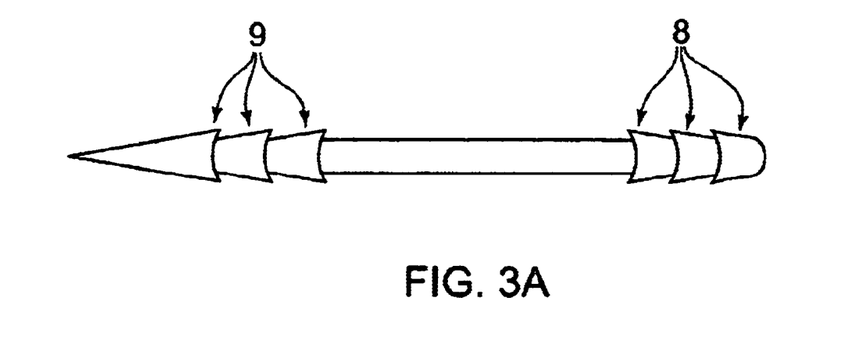
Figure 3B:
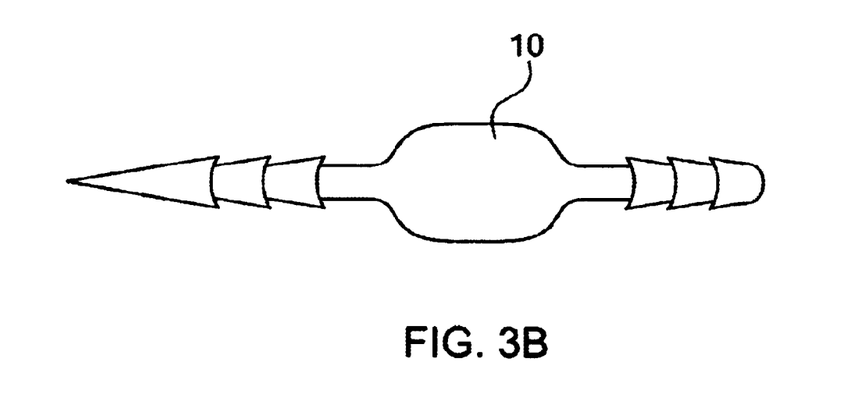
FIG. 3B illustrates, as viewed from above, another embodiment of the present invention having proximal and distal, ridge-like protrusions and whose middle part has been flattened, so that the fastener has a cross-like profile when viewed from the direction of the distal tip of the fastener, according to FIG. 3C.
Figure 3C:
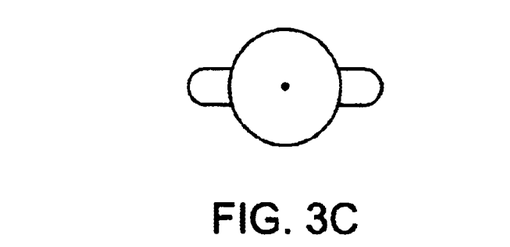

FIG. 3A illustrates, as viewed longitudinally from the side and FIG. 3B illustrates, as viewed from above, a fastener which has proximal and distal, ridge-like protrusions (8,9) and whose middle part 10 has been flattened, so that the fastener has a cross-like profile when viewed from the direction of the distal tip of the fastener, according to FIG. 3C. This type of fastener allows for excellent guidance inside of an installation cannula whose inner cross-section corresponds to the cross section of the fastener according to FIG. 3C.

Figure 4A:
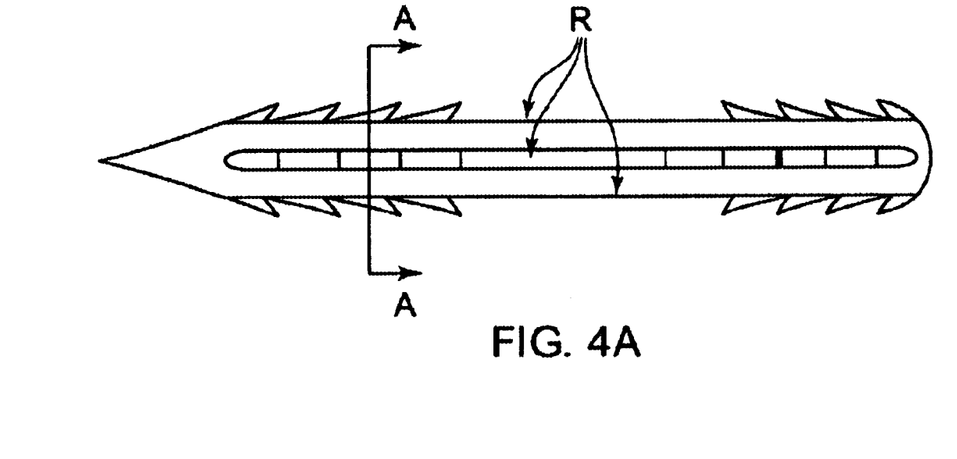
FIG. 4A illustrates another embodiment of the present invention, from a side-view perspective, having on its surface four longitudinal ridges (R), which are arranged onto the surface of the fastener according to FIG. 4B which gives the cross-section of the fastener in the plane A—A of FIG. 4A.

The surface of the fastener can also include longitudinal ridges, into which the arresting means can be machined or molded. FIG. 4A shows a side-view perspective of such a fastener having on its surface four longitudinal ridges (R), which are arranged onto the surface of the fastener according to FIG. 4B which gives the cross-section of the fastener in the plane A—A of FIG. 4A.

Figure 4B:
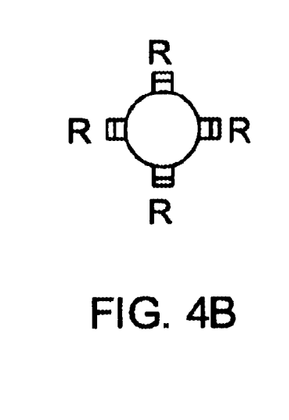

The proximal and distal protrusions (like barbs) can be machined effectively into the longitudinal ridges.

Figure 5:
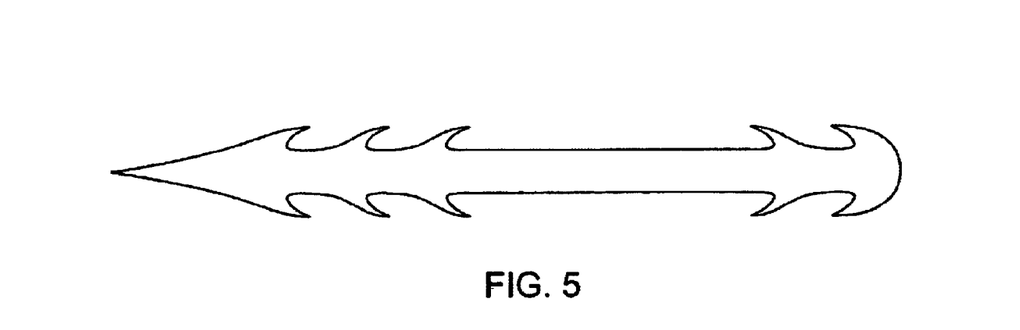
FIG. 5 illustrates an embodiment of the present invention wherein the slopes of protrusions are curved.
Figure 6:
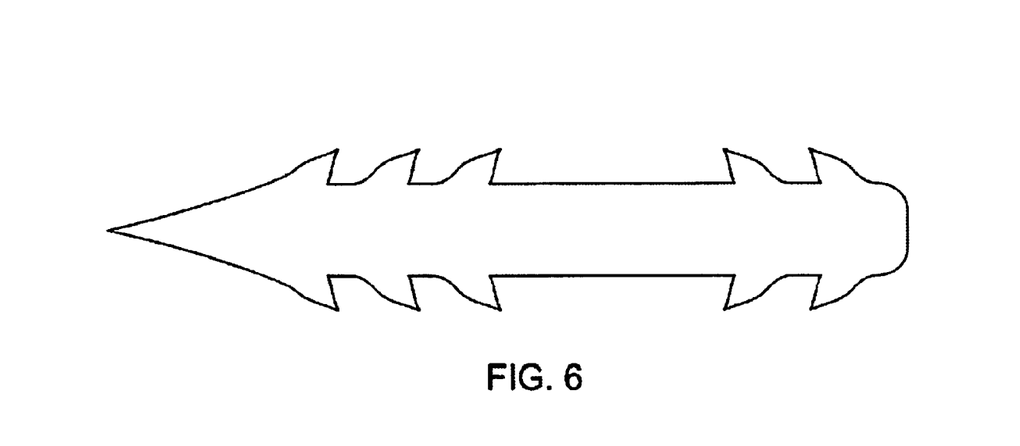
FIG. 6 illustrates an embodiment of the present invention wherein the protrusions are stiff and sharp-pointed.
Figure 7:
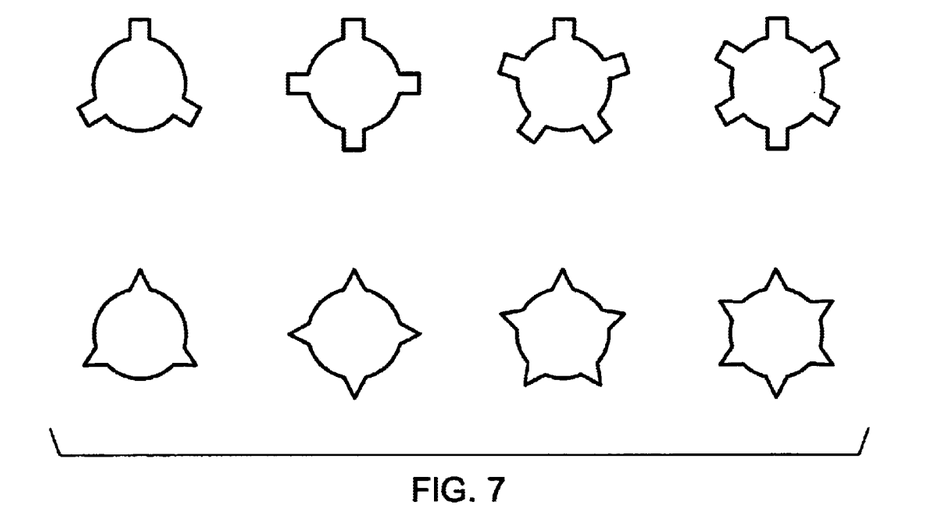
FIG. 7 illustrates an embodiment of the present invention showing an arrangement and geometry of cross-sectional structures of ridged fasteners.
Figure 8:
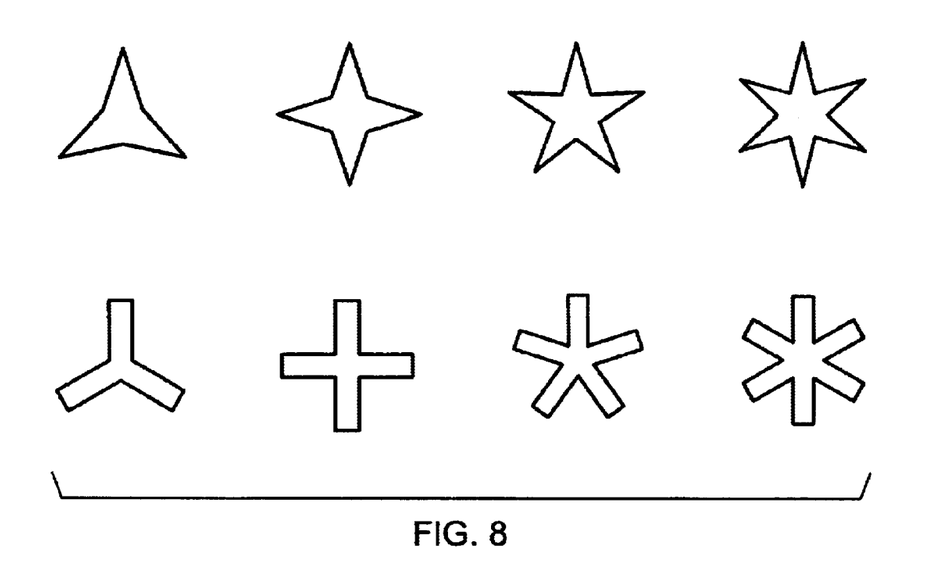
FIG. 8 illustrates an embodiment of the present invention showing another arrangement and geometry of cross-sectional structures of ridged fasteners.
Figure 9:
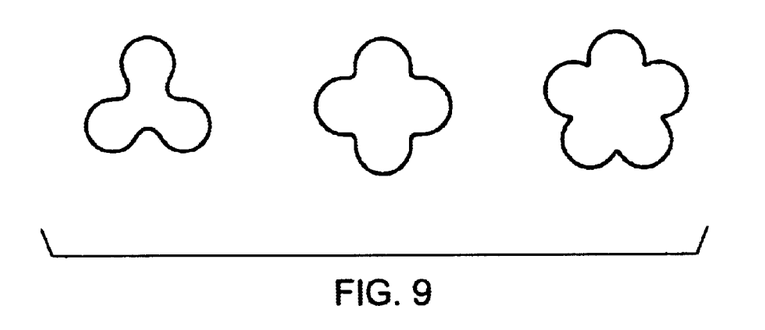
FIG. 9 illustrates an embodiment of the present invention showing another arrangement and geometry of cross-sectional structures of ridged fasteners.
Figure 10:
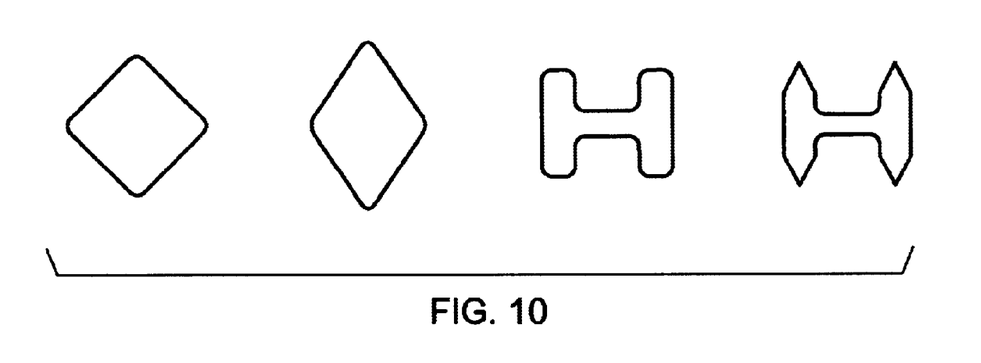
FIG. 10 illustrates an embodiment of the present invention showing yet another arrangement and geometry of cross-sectional structures of ridged fasteners.

It is evident that other types of proximal and distal protrusions, than those described in FIGS. 1–4, can be used in the fasteners of the invention. E.g., both of the slopes of protrusions can be curved, as is illustrated in FIG. 5. The protrusions can also be both stiff and sharp-pointed as is illustrated in FIG. 6.

There are numerous possible arrangements for the longitudinal ridges on the surface of the fastener. Also the geometry of the ridges can be varied to influence the gripping capacity of barbs or other protrusions inside of meniscal or other soft tissue. FIGS. 7–10 illustrate some preferred embodiments of the cross-sectional structures of ridged fasteners.

Figure 11A:
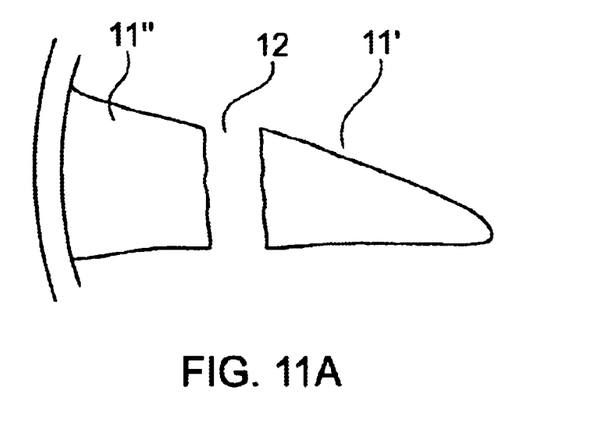
FIG. 11A illustrates, as viewed from the side, a meniscus with a rupture, separating the meniscus into a proximal side and a distal side.
Figure 11B:
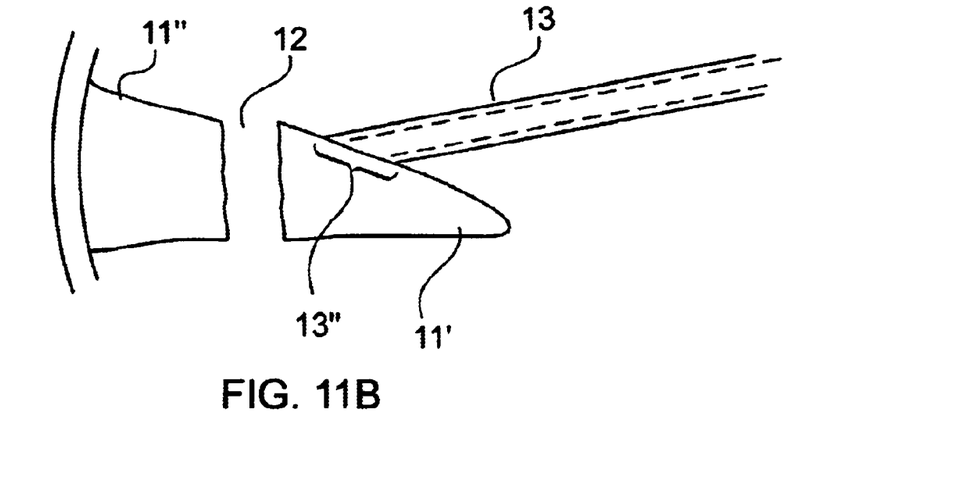
As seen in FIG. 11B, during the operation the tip of a cannula is pushed into the knee joint through a small incision.

FIGS. 11A–D illustrate a preferred method for installing fasteners of the invention into ruptured meniscal tissue. FIG. 11A illustrates, as viewed from the side, a meniscus with a rupture, 12, separating the meniscus into a proximal side, 11', and a distal side, 11". As seen in FIG. 11B during the operation the tip, 13" of a cannula 13 is pushed into the knee joint through a small incision and the tip is located on the surface of the proximal part of the meniscus 11' (in relation to the rupture 12).

Figure 11C:
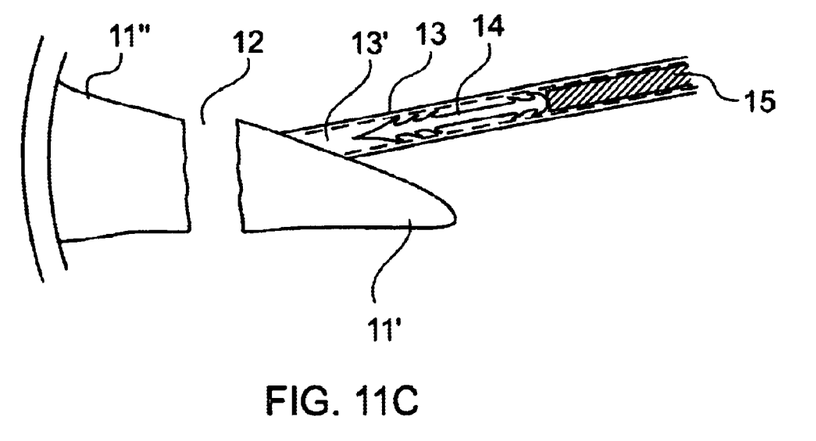
As seen in FIG. 11C, a piston moves to the left (distally) and pushes the fastener through the hole inside of the cannula. The piston can be accelerated to a high speed so that the piston pushes the fastener with a high speed into the meniscus as is illustrated in FIG. 11D.
Figure 11D:
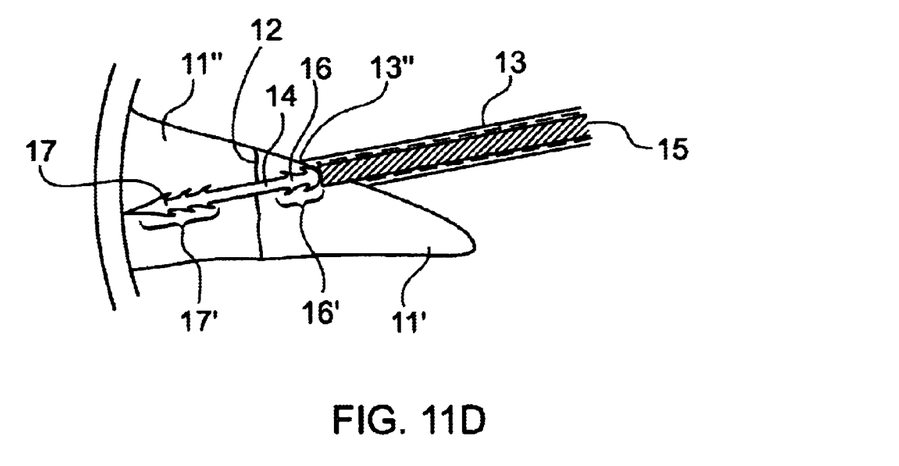

As seen in FIG. 11C, piston 15 moves to the left (distally) and pushes the fastener 14 through the hole 13' inside of cannula 13. The piston 15 can be accelerated to a high speed so that the piston 15 pushes (shoots) the fastener 14 with a high speed into the meniscus as is illustrated in FIG. 11D. The piston 15 stops at the final stage of its movement (by way of, e.g., a stopper [not shown] at the proximal end of the piston 15), typically so that the tip of the piston protrudes out of the tip 13" of cannula 13 ca. 0.5–1 mm, to push the fastener totally inside of the meniscal tissue. When the location of the cannula tip 13" on the meniscal surface is selected in a proper way, typically 2–4 mm in front of the meniscal tear 12, and the direction of the cannula is proper, the fastener penetrates the proximal meniscus part 11', the tear plane 12 and closes the tear with the compression force created with the installation push. According to FIG. 11D the piston 15 pushes and forces the fastener 14 totally inside of the meniscal tissue. When the proximal portion 16 of the fastener is forced inside of the meniscal tissue, the proximal protrusions 16' create the pushing force into the proximal part of meniscus 11', closing the rupture 12. As soon as the piston 15 stops (typically 0.5–1 mm below the surface of the meniscus) the proximal protrusions 16' stop the fastener and prevent its further movement into meniscal tissue. On the other hand, the distal portion of the device 17 is pushed across the rupture 12 and into the distal side of the meniscus 11", where the distal protrusions 17' prevent the slipping of the fastener back in the direction opposite to the installation direction. Accordingly, the rupture 12 is closed effectively, the fastener is locked to its position to keep the rupture 12 closed and the whole fastener has been buried inside of meniscal tissue to eliminate the risks related to implant parts located on the surface of the meniscus.

It is typical that the microstructure of a meniscus contains reinforcing collagen fibers. Inside of a meniscus, many collagen fibers are oriented in a horizontal plane nearly parallel to the lower surface of the meniscus. If the horizontal collagen fibers are examined in a cut cross-section of a meniscus (as shown in FIGS. 11–11D) their cut ends can be seen microscopically as points on the cross-sectional surface, according to FIG. 12. The typical vertical meniscus lesion (rupture) 12 develops along the long axes of collagen fibers, because the binding forces between collagen fibers are relatively weak.

Figure 13:
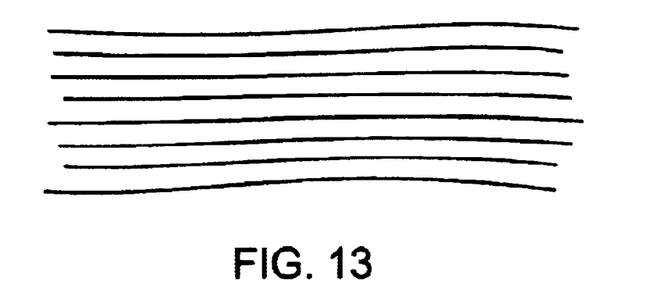
FIG. 13 illustrates parallel, horizontal fiber bundles.
Figure 14:
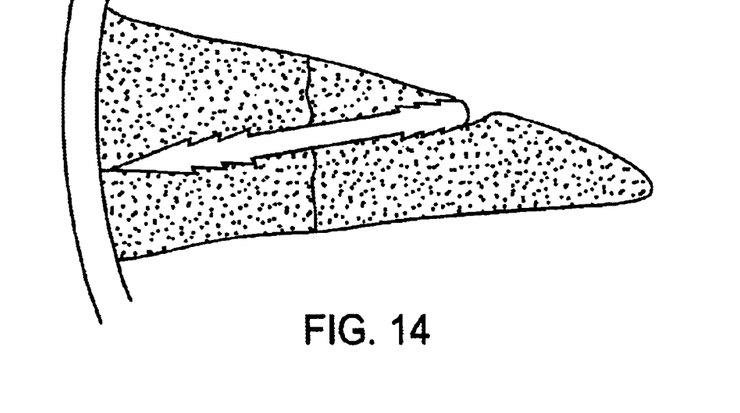

If the internal collagen fiber structure of a meniscus is examined from the direction of the long axis of the fastener, i e. from the direction from which the fastener enters the meniscus, the collagen fibers are seen as parallel, horizontal fiber bundles, as is shown schematically in FIG. 13.

Figure 12:
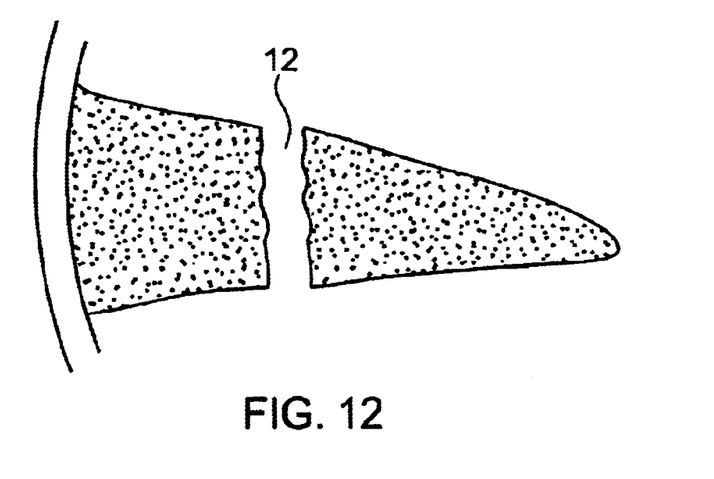
Figure 15:
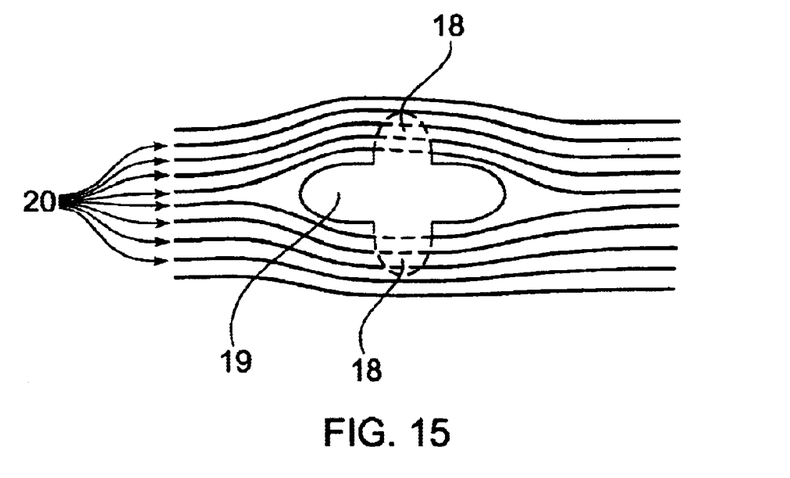

Because of the special arrangement of reinforcing horizontal collagen fibers inside of the meniscus, shown schematically in FIGS. 12 and 13, it is important that the protrusions are located at least on the upper and lower surfaces of the proximal and distal portions of the fastener, so that as the fastener penetrates into the meniscal tissue, the protrusions grab the horizontal collagen fiber bundles, locking the fastener in place. This is shown schematically in FIG. 14 as a meniscal cross-section. In FIG. 15 the fastener—horizontal collagen fiber relationship is viewed from the direction from which the fastener enters the meniscus, showing how the protrusions 18, protruding from the upper and lower surfaces of the shaft of the fastener 19, lock themselves effectively between horizontal collagen fibers 20.

Of course, it is well known that the meniscus also includes oriented fibers that are not horizontal. For example, the meniscus can also contain fibers having radial or oblique orientations. The collagen fibers form an essentially three-dimensional network in the meniscus, with the horizontal fibers being of particular importance with regard to using the present invention for treating the typical vertical (bucket handle) tears that occur.

The bioabsorbable implants of this invention can be manufactured of bioabsorbable polymers, copolymers or polymer mixtures or alloys with melt molding methods known in the prior art. It is also possible to use the techniques of U.S. Pat. No. 4,743,257 to mold in a compression or injection mold absorbable fibers and binding polymer together to create a fiber-reinforced or especially a self-reinforced structure. The implants of this invention can be molded in a single compression molding cycle, or the protrusions can be machined on the surface of a fastener after the molding cycle.

The oriented or self-reinforced structure can also be created during extrusion or injection molding of absorbable polymeric melt through a suitable die or into a suitable mold at high speed and pressure. When cooling occurs at suitable conditions, the flow orientation of the melt remains in the solid material as an oriented or self-reinforcing structure. In an advantageous embodiment, the mold can have the form of the implant, but it is also possible to manufacture the implants of the invention by machining (possibly using heat) injection-molded or extruded semifinished products.

It is advantageous to make the implants of melt-molded, solid state drawn or compressed, bioabsorbable polymeric materials, which are described e.g. in U.S. Pat. Nos. 4,968,317 or 4,898,186.

The reinforcing fibers of the implant can also be ceramic fibers, like bioabsorbable hydroxyapatite or bioglass fibers. Such bioabsorbable, ceramic fiber reinforced materials are described e.g. in European Patent Application No. 0146398 and in WO 96/21628.

The oriented or self-reinforced or otherwise fiber reinforced implants of this invention can be manufactured by molding the reinforcement fiber-polymer matrix to the final product in a mold, whose mold cavity has the form of the final product or the final form can be machined mechanically (possibly also using heat) on a preform, such as a melt-molded and solid-state drawn rod, as is described e.g. in U.S. Pat. No. 4,968,317.

In some advantageous embodiments of this invention, the orientation and/or reinforcing elements of the self-reinforced structure are mainly oriented in the direction of the long axis of the shaft of the implant. The reinforcement elements may extend into any protrusions or ridges of the implant. The reinforcement elements can also turn spirally around the long axis of the implant. Also other different orientations of reinforcement elements in elongated samples which are familiar from composite technology can be applied to the present invention. However, a general feature of orientation, fiber-reinforcement or self-reinforcement of the implants of this invention is that many of the reinforcing elements are oriented in such a way that they can carry effectively the different external loads (such as tensile, bending and shear loads) that are directed to the healing rupture (for example, loads to a meniscus caused by the movements of the patient's knee).

According to an advantageous embodiment of the invention, the meniscal repair implant, or a special coating layer on its surface, may contain one or more bioactive substances, such as antibiotics, chemotherapeutic substances, angiogenic growth factors, substances accelerating the healing of the wound, growth hormones and the like. Such bioactive meniscal repair implants are especially advantageous in surgical use, because they chemically contribute to the healing of the lesion in addition to providing mechanical support.

The oriented and/or reinforced materials of the implants typically have tensile strengths of 100–2000 MPa, bending strengths of 100–600 MPa and shear strengths of 80–400 MPa. Additionally, they are usually stiff and tough. These mechanical properties are superior to those of non-reinforced absorbable polymers which typically show strengths between 40 and 100 MPa and are additionally either very flexible or brittle (see e.g. Ref 3S Vainionpaa, P. Rokkanen and P. Tormala, "Surgical Applications of Biodegradable Polymers in Human Tissues", Progr. Polym. Sci 14/1989, pp.679–716).

The implants of the present invention may be sterilized by any of the well known sterilization techniques, depending on the type of material used in manufacture of the implant. Suitable sterilization techniques include heat or steam sterilization, radiation sterilization such as cobalt 60 irradiation or electron beams, ethylene oxide sterilization, and the like.

After the description above of the present invention and certain specific embodiments thereof, it will be readily apparent to those skilled in the art that many variations and modifications may be made to the present invention without departing from the spirit and scope thereof

What is claimed is:

1. A surgical fastener for repairing tissue comprising:
a shaft having a longitudinal axis and including proximal and distal portions, said proximal portion having a blunt tip and comprising at least one protrusion configured to resist movement in the distal direction, said distal portion having a pointed tip and comprising at least one protrusion configured to resist movement in the proximal direction and configured to permit movement of the shaft in the distal direction said shaft comprising a plurality of longitudinal ridges, each longitudinal ridge defining a channel that extends from the proximal portion to the distal portion, wherein said fastener is capable of being pushed from behind so that the fastener is located entirely within said tissue to be repaired.

2. A surgical fastener of claim 1, wherein the fastener contains a bioactive material.

3. A surgical fastener of claim 1, wherein the fastener comprises a oriented or reinforced polymer having tensile strengths of 100–2000 MPa.

4. A surgical fastener of claim 1, wherein at least one of said proximal protrusion protrudes farther from said shaft than said distal protrusion.

5. A surgical fastener of claim 1, wherein at least one of said distal protrusion and said proximal protrusion is molded or machined into at least one of the plurality of longitudinal ridges.

6. A surgical fastener of claim 1, wherein at least one of said proximal protrusions and said distal protrusion on said shaft comprises spikes or barbs.

7. A surgical fastener of claim 1, wherein the angle formed between a tangent to the distal surface of the distal protrusion and the shaft, in the proximal direction, is less than 45°, the angle formed between a tangent to the proximal surface of the distal protrusion and the shaft, in the proximal direction, is less than 90°, and the angle formed between a tangent to the distal surface of the proximal protrusion and the shaft, in the proximal direction, is greater than 90°.

8. A surgical fastener for repairing a tear in a meniscus comprising:
a shaft having a longitudinal axis and proximal and distal portions, said proximal portion having a blunt tip and comprising at least one protrusion configured to resist movement in the distal direction, said distal portion having a pointed tip and comprising at least one protrusions configured to resist movement in the proximal direction and configured to permit the movement of the shaft in the distal direction, said shaft comprising a plurality of longitudinal ridges, each longitudinal ridge defining a channel that extends from the proximal portion to the distal portion of the shaft, wherein said fastener is capable of being pushed from behind so that the fastener is located in its entirety within the meniscus.

9. A method of repairing a tear in a meniscus, comprising the steps of:
aligning the fastener of claim 8 on the surface of the meniscus;
positioning the fastener into the meniscus by pushing the said fastener into the meniscus from behind so that the fastener bridges and closes the tear and the fastener is located in its entirety within the meniscus.

* * * * *